United States Patent [19]

Chan

[11] Patent Number: 5,741,265

[45] Date of Patent: Apr. 21, 1998

[54] BONE CANAL PRESSURIZER

[76] Inventor: Kwan-Ho Chan, 4803 1st Pl., Lubbock, Tex. 79416

[21] Appl. No.: 604,179

[22] Filed: Feb. 21, 1996

[51] Int. Cl.⁶ ........................................................ A61F 2/28
[52] U.S. Cl. ............................. 606/94; 606/92; 606/93
[58] Field of Search ............................... 606/94, 93, 92, 606/95

[56] References Cited

U.S. PATENT DOCUMENTS

| | | | |
|---|---|---|---|
| 4,274,163 | 6/1981 | Malcom et al. | 606/94 |
| 4,488,549 | 12/1984 | Lee et al. | 606/95 |
| 4,815,454 | 3/1989 | Dozier et al. | 606/94 |
| 4,896,662 | 1/1990 | Noble | 606/94 |
| 5,061,287 | 10/1991 | Feiler | 606/92 |
| 5,501,687 | 3/1996 | Willert et al. | 606/94 |
| 5,507,749 | 4/1996 | Draenert | 606/94 |

Primary Examiner—Michael Buiz
Assistant Examiner—Julian W. Woo
Attorney, Agent, or Firm—Pandiscio & Pandiscio

[57] ABSTRACT

A bone canal pressurizer is disclosed which comprises a body made out of a soft foam material. This body has a planar proximal surface and a planar distal surface, with the proximal surface having a greater surface area than the distal surface, and with an inclined side wall extending between the proximal surface and the distal surface. A bore extends through the body, opening on both the proximal surface and the distal surface. This bore is sized so as to have a diameter smaller than the outer diameter of a cement dispenser's nozzle. The entryway to the bore is preferably chamfered about the proximal surface. A rigid plate is fixed to the proximal surface of the soft foam body, and includes a hole extending therethrough. This hole is aligned with the bore extending through the pressurizer's soft foam body, and is sized so as to have a diameter larger than the outer diameter of a cement dispenser's nozzle. The distal surface of the body is sized so as to be small enough to fit within the bone canal of a bone, and the rigid plate is sized so as to be larger than the bone canal of that same bone. A method of using the bone canal pressurizer to deploy cement into a bone canal is also disclosed.

11 Claims, 6 Drawing Sheets

1

BONE CANAL PRESSURIZER

FIELD OF THE INVENTION

This invention relates to surgical apparatus and procedures in general, and more particularly to bone canal pressurizers of the sort used in conjunction with bone cement dispensers to compact bone cement into bone canals during total joint replacement surgeries.

BACKGROUND OF THE INVENTION

Bone canal pressurizers are well known in the art. These devices are generally used in conjunction with bone cement dispensers to compact bone cement into a bone canal before fixing a prosthetic device in that bone canal. By way of example, bone canal pressurizers are frequently used in conjunction with bone cement dispensers to compact bone cement into the intramedullary canal of the femur before fixing the femoral stem of an artificial hip in that canal.

More particularly, it has generally been found that a prosthetic device will be more securely fixed in a bone canal if the bone cement is well packed into the bone canal before the prosthetic device is positioned in the bone canal. To this end, after initial preparation and cleaning of the bone canal, the distal end of the canal is occluded with a plug. The bone cement is then injected into the most distal part of the bone canal using a bone cement dispenser having a long nozzle. See, for example, FIG. 1, where the nozzle 5 of a cement dispenser 10 is shown deploying cement 15 into the distal end of the intramedullary canal 20 of a femur 25, adjacent to a distal plug 30. The bone canal is filled with bone cement in a retrograde fashion, by withdrawing the nozzle of the cement dispenser from the distal end of the bone canal to the proximal end of the bone canal as the cement issues from the nozzle. Such retrograde filling avoids trapping air in the distal part of the bone canal.

After the bone canal is filled with bone cement, a bone canal pressurizer is then connected to the bone cement dispenser. The pressurizer is pressed against the open end of the bone to occlude the bone canal. More cement is then injected into the bone canal through the pressurizer and under pressure. Under such pressurization, the cement in the bone canal will intrude into the interstices of the inner surface of the bone canal. When the bone cement thereafter sets, a micro-interlock will be established between the cement and the irregularities of the interior surface of the bone canal. This significantly enhances fixation of the prosthetic device in the bone canal.

It is also to be appreciated that, in addition to limiting the volume into which the bone cement is injected, and thus permitting the cement to be injected under pressure, the pressurizer also serves to prevent bone cement from accidentally spilling out of the open end of the patient's bone and about the surgical site.

One well known bone canal pressurizer is the so-called Miller pressurizer. Looking next at FIG. 2, a Miller pressurizer 100 is shown attached to cement dispenser 10. The Miller pressurizer 100 comprises a stiff silicone body 110. A hole 115 extends through this body, substantially centrally thereof. The Miller pressurizer 100 is secured to the distal end of the cement dispenser using a screw mount so that the pressurizer's hole 115 is in communication with the interior of the cement dispenser. The exterior of the pressurizer's stiff silicone body is sized so as to make a tight fit within the open end of the bone canal, e.g., the intramedullary bone canal 20 of femur 25.

The Miller pressurizer is generally used as follows. First, bone canal 20 is filled with cement 15 in the retrograde fashion previously described, using long nozzle 5 attached to cement dispenser 10. Then long nozzle 5 is dismounted from cement dispenser 10 and the Miller pressurizer 100 is mounted on the cement dispenser in its place. Next, the Miller pressurizer 100 is pressed against the open end of bone 25 so that the Miller pressurizer seats in, and seals off, the open end of the bone's intramedullary canal 20. It is to be appreciated that the Miller pressurizer 100 will generally make a tight fit with bone 25 as the stiff silicone body 110 of the pressurizer is forced down into, and seats in, the interior of the bone canal. Cement dispenser 10 is then used to force additional cement 15 into bone canal 20 under pressure so as to effect cement compacting and cement intrusion.

While the aforementioned Miller pressurizer is generally capable of making a satisfactory seal between the pressurizer and the bone, it does suffer from a number of disadvantages. First, it's use requires that long nozzle 5 (which is needed to deploy cement at the distal end of bone canal 20) be dismounted from cement dispenser 10 before the Miller pressurizer 100 is mounted in its place. This can be inconvenient. Second, since the Miller pressurizer is formed out of a stiff silicone material, it has a limited degree of resiliency. This means that a particular pressurizer may properly seal off a bone of one size but not a bone of another size. As a result, it is generally necessary to provide the surgeon with a set of Miller pressurizers having a range of different sizes, so that the surgeon can select an appropriately sized pressurizer for a given patient and procedure. Third, the pressurizer's stiff silicone body may have difficulty effectively sealing off a bone where that bone has an unusual anatomical configuration. Fourth, since the Miller pressurizer sits partially within the interior of the bone canal, it prevents the very proximal edge of the bone canal from being filled with pressurized cement. This can undermine optimum fixation of the prosthesis to the bone. And fifth, the construction of the Miller pressurizer does not permit the surgeon to adjust the orientation of the cement dispensing apparatus while under seal so as to avoid impingement of the cement dispenser against a surrounding bony or soft tissue obstruction.

Another well known bone canal pressurizer is the so-called Harris pressurizer. Looking next at FIG. 3, a Harris pressurizer 200 is shown. It generally comprises a short nozzle 205 which terminates at its distal end in a flange 210. Flange 210 comprises a flat distal surface 215. A soft foam pad 220 is fixed to distal surface 215 of flange 210. A central hole 225 extends through pressurizer 200. Central hole 225 extends through flange 210 and pad 220, and communicates with the interior of the cement dispenser when the Harris pressurizer is mounted on the front of the cement dispenser using a screw mount (not shown). Flange 210 and pad 220 are sized so as to engage and envelop the open end of a bone, e.g. the open end of femur 25.

The Harris pressurizer is generally used as follows. First, bone canal 20 is filled with cement 15 in the retrograde fashion previously described, using long nozzle 5 attached to cement dispenser 10. Then long nozzle 5 is dismounted from cement dispenser 10 and the Harris pressurizer 200 is mounted on the cement dispenser in its place. Next, the Harris pressurizer 200 is pressed against the open end of bone 25 so that the pressurizer's soft foam pad 220 seats against, and seals off, the end surface of the bone. Holding the cement dispenser 10 tightly against the end of the bone, the cement dispenser is then used to force additional cement 15 into bone canal 20 under pressure so as to effect cement compacting.

The Harris pressurizer improves upon the Miller pressurizer in some ways. For one thing, a single Harris pressurizer is generally capable of being used with a fairly broad range of bone sizes, so it is not necessary to provide the surgeon with a set of pressurizers having a range of different sizes. Also, since the Harris pressurizer is placed against the outer surface of the bone and does not extend down into the bone canal in the manner of the Miller pressurizer, the Harris pressurizer does not prevent the very proximal edge of the bone canal from being filled with pressurized cement.

Unfortunately, however, the Harris pressurizer also suffers from a number of disadvantages. First, the Harris pressurizer also requires that long nozzle 5 (which is needed to deploy cement at the distal end of bone canal 20) be dismounted from cement dispenser 10 before the Harris pressurizer 200 is mounted in its place. Second, since the Harris pressurizer is manually held against the outer surface of the bone, it makes a less secure seal with the bone than the Miller pressurizer. Third, since the soft foam pad 220 and the underlying flat distal surface 215 of the Harris pressurizer's flange 210 must rest against the flat end of bone 25, the orientation of the Harris pressurizer is substantially fixed relative to the bone. Thus, the construction of the Harris pressurizer does not permit the surgeon to adjust the orientation of the cement dispensing apparatus while under seal so as to avoid impingement of the cement dispenser against a surrounding bony or soft tissue obstruction.

Thus, there is presently a need for an improved bone canal pressurizer which is convenient to use, and which can provide a reliable seal between the pressurizer and the bone, and between the pressurizer and the cement dispenser, yet still permit maneuvering of the cement dispensing apparatus relative to the bone.

OBJECTS OF THE INVENTION

Accordingly, one object of the present invention is to provide an improved bone canal pressurizer which is convenient to use.

Another object of the present invention is to provide an improved bone canal pressurizer which is adapted to make an effective seal with a bone, whereby the pressurizer can serve to seal off the open end of a bone canal into which bone cement is to be injected under pressure.

And another object of the present invention is to provide an improved bone canal pressurizer which is adapted to fit around, and make an effective seal with, the nozzle of a bone cement dispenser, whereby the nozzle of the bone cement dispenser can be used to inject bone cement, under pressure, into the interior of a bone canal.

Still another object of the present invention is to provide an improved bone canal pressurizer which facilitates angular movement of the cement dispenser and its nozzle to avoid soft tissue and/or bony obstructions even while the pressurizer is sealing off the open end of a bone.

Yet another object of the present invention is to provide an improved bone canal pressurizer which is adapted to fit around the nozzle of a bone cement dispenser and which can provide a reliable seal between the pressurizer and a bone, and between the pressurizer and the cement dispenser's nozzle, yet still permit maneuvering of the nozzle relative to both the pressurizer and the bone.

And another object of the present invention is to provide an improved bone canal pressurizer wherein a single pressurizer can be used in conjunction with a variety of different bone sizes and shapes, so as to eliminate the need to provide the surgeon with a set of pressurizers having a range of different sizes.

And another object of the present invention is to provide an improved method for dispensing bone cement into the interior of a bone canal under pressure.

SUMMARY OF THE INVENTION

These and other objects of the present invention are addressed by the provision and use of a novel bone canal pressurizer.

The novel bone canal pressurizer comprises a body made out of a soft foam material. This body has a planar proximal surface and a planar distal surface, with the proximal surface having a greater surface area than the distal surface, and with an inclined side wall extending between the proximal surface and the distal surface. A bore extends through the body, opening on both the proximal surface and the distal surface. This bore is sized so as to have a diameter smaller than the outer diameter of a cement dispenser's nozzle. The entryway to the bore is preferably chamfered about the proximal surface. A rigid plate is fixed to the proximal surface of the soft foam body, and includes a hole extending therethrough. This hole is aligned with the bore extending through the pressurizer's soft foam body, and is sized so as to have a diameter larger than the outer diameter of a cement dispenser's nozzle.

In one manner of use, the bone canal pressurizer is used as follows. First, the nozzle of the cement dispenser is passed through the pressurizer's hole and bore so that the distal end of the nozzle protrudes from the distal end of the pressurizer and the pressurizer sits adjacent to the body of the cement dispenser, with the nozzle of the cement dispenser substantially fully exposed. The pressurizer is kept mounted on the proximal end of the nozzle while the nozzle is used to fill the bone canal with cement in the retrograde fashion previously described. When the bone canal is substantially completely filled with cement, the pressurizer is slid distally down the length of the nozzle's shaft to engage the open end of the bone. In particular, the nozzle is placed against the open end of the bone so that (i) the pressurizer's distal surface resides inside the bone canal, (ii) the pressurizer's inclined side wall engages the end surface of the bone, and (iii) the pressurizer's bore and hole are generally aligned with the longitudinal axis of the bone canal. Pressure thereafter manually applied to the pressurizer's rigid plate will keep the pressurizer's soft inclined side wall in sealing engagement with the end surface of the bone. At the same time, the soft body of the pressurizer will make a tight seal about the cement dispenser's nozzle. Thus, additional bone cement may then be directed into the interior of the bone canal under pressure, without cement spilling out between the pressurizer and the bone or between the pressurizer and the nozzle.

Significantly, since the diameter of the hole in the pressurizer's rigid plate is oversized relative to the outer diameter of the nozzle, and since the body of the pressurizer is formed out of soft foam, the surgeon may move the distal tip of the nozzle about, without undermining the integrity of the pressurizer's seal with the bone or the pressurizer's seal with the nozzle of the cement dispenser, so as to avoid soft tissue or bony obstructions while injecting cement into the bone canal under pressure.

In an alternative manner of use, the pressurizer is left initially dismounted from the nozzle of the bone cement dispenser while the nozzle is used to fill the bone canal with cement in the traditional retrograde manner described above. After the canal has been filled with cement, the nozzle of the cement dispenser is withdrawn from the bone canal. The nozzle of the pressurizer is then preferably shortened in length by snapping off the distal end of the nozzle using score lines which are provided for this purpose. Then the pressurizer is mounted on the shortened nozzle, and the bone cement dispenser and pressurizer are moved as a unit toward the open end of the bone, whereby the distal end of the nozzle may be positioned within the proximal end of the bone canal while the pressurizer is seated against, and seals off, the open end of the bone. The cement dispenser may then be used to inject additional cement into the bone canal under pressure.

BRIEF DESCRIPTION OF THE DRAWINGS

These and other objects and features of the present invention will be more fully disclosed or rendered obvious by the following detailed description of the preferred embodiment of the invention, which is to be considered together with the accompanying drawings wherein like numbers refer to like parts, and further wherein.

DETAILED DESCRIPTION OF THE PREFERRED EMBODIMENT

Figure 1:
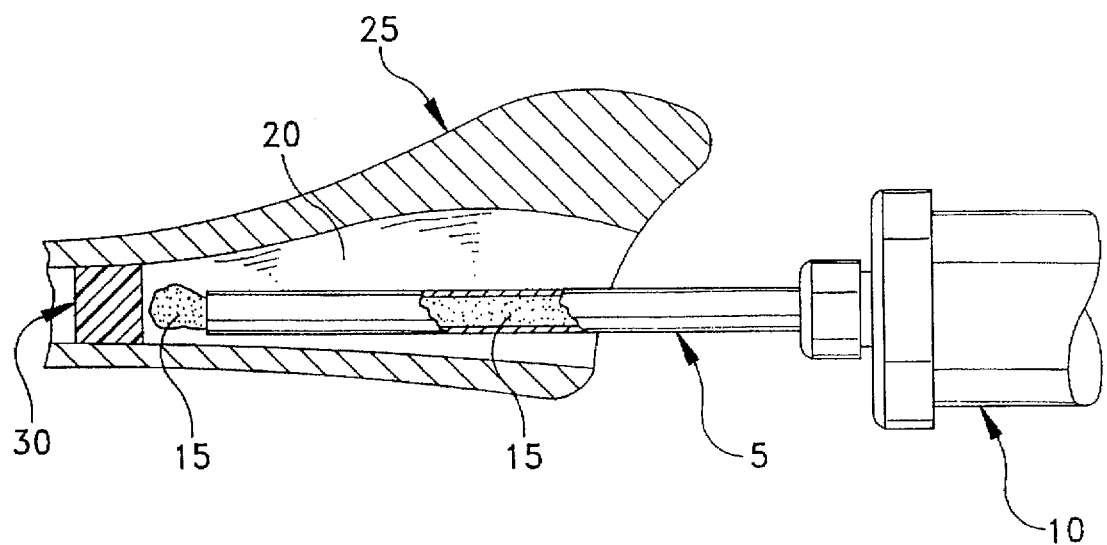
FIG. 1 is a schematic side view, partially in section, showing a bone cement dispenser filling a bone canal with cement in the traditional retrograde fashion.
Figure 2:
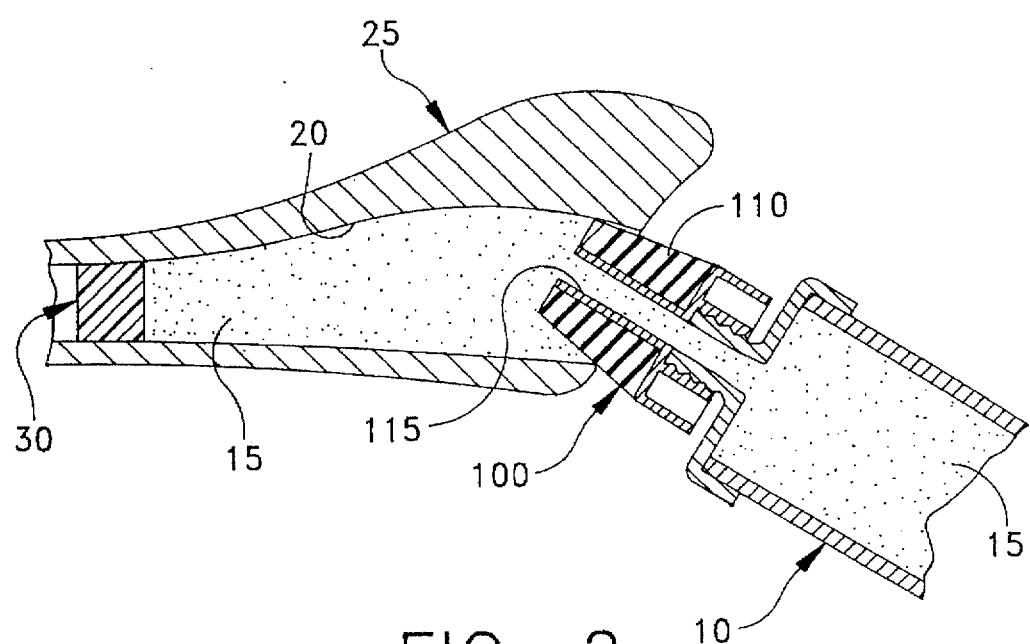
FIG. 2 is a schematic side view, partially in section, showing a Miller pressurizer being used to pressurize bone cement in a bone canal.
Figure 3:
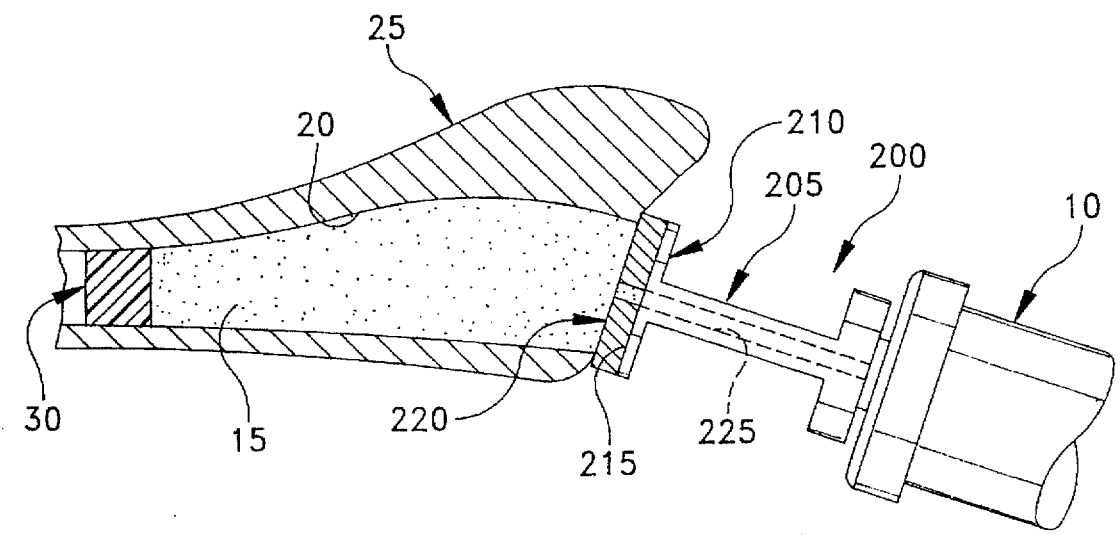
FIG. 3 is a schematic side view, partially in section, showing a Harris pressurizer being used to pressurize bone cement in a bone canal.
Figure 4:
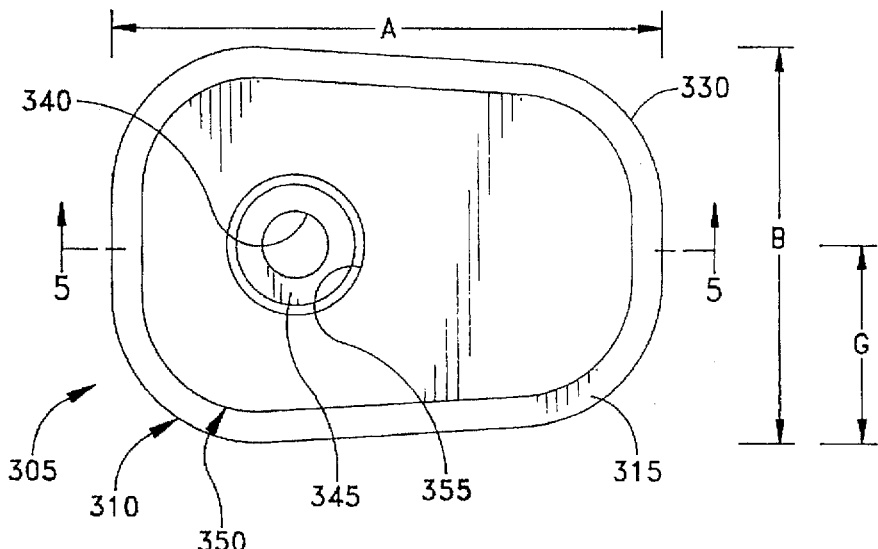
FIG. 4 is a top plan view showing a bone canal pressurizer formed in accordance with the present invention.
Figure 5:
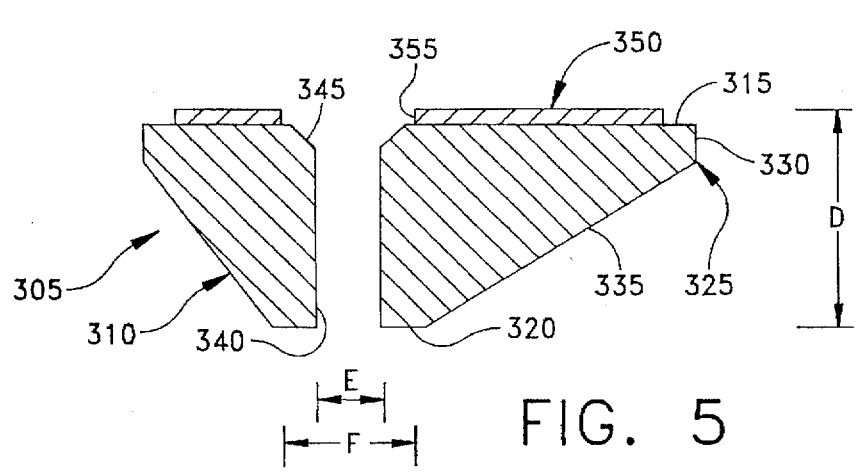
FIG. 5 is a side view, in section, taken along line 5—5 of FIG. 4.
Figure 6:
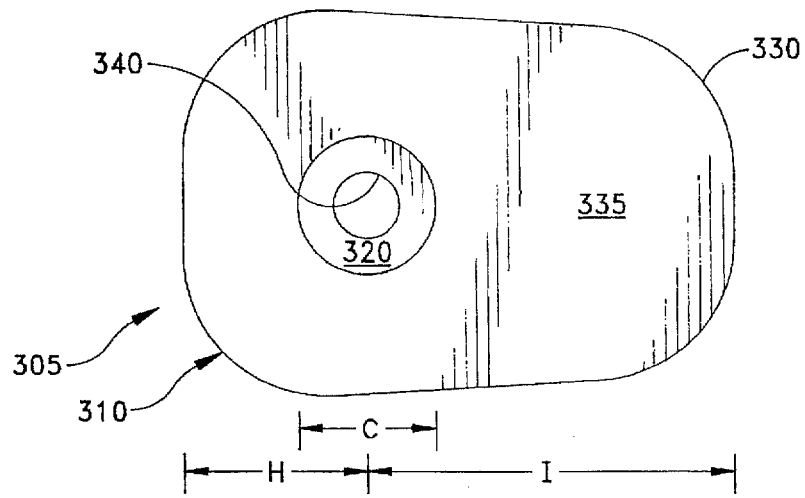
FIG. 6 is a bottom plan view showing the bone canal pressurizer of FIGS. 4 and 5.

Looking next at FIGS. 4-6, a bone canal pressurizer 305 is shown which comprises the preferred embodiment of the present invention.

Pressurizer 305 comprises a body 310. Body 310 is formed out of a soft, relatively dense, resilient foam material of the sort well known in the art. By way of example but not limitation, body 310 might be formed out of a closed cell polyethylene foam or a closed cell Silastic silicone foam.

Body 310 comprises a planar proximal surface 315 and a planar distal surface 320. Proximal surface 315 has a greater surface area than distal surface 320. Proximal surface 315 has a generally trapezoidal configuration, with the corners thereof rounded off. Distal surface 320 preferably has a generally rounded, and preferably circular, configuration. An inclined side wall 325 extends between proximal surface 315 and distal surface 320. Inclined side wall 325 generally comprises a vertical (as seen from the angle of view of FIG. 5) portion 330 adjoining proximal surface 315, and an inclined portion 335 extending between vertical portion 330 and distal surface 320.

A bore 340 extends through body 310, opening on both proximal surface 315 and distal surface 320. Bore 340 is sized so as to have a diameter smaller than the outer diameter of a cement dispenser's nozzle, as will hereinafter be disclosed in further detail. Bore 340 is preferably provided with a chamfered entryway 345 (best seen in FIG. 5) adjacent to proximal surface 315.

A rigid plate 350 is fixed to proximal surface 315. Rigid plate 350 is preferably formed out of a hard, rigid material such as a biocompatible polymer or metal of the sort well known in the art. By way of example but not limitation, rigid plate 350 might be formed out of plastic (such as polyethylene) or out of stainless steel. Rigid plate 350 can be fixed to proximal surface 315 using double-sided tape, another type of adhesive, ultrasonic welding, or by interdigitation of prongs protruding from the undersurface of the rigid plate, or by other means well known in the art. Rigid plate 350 has a generally trapezoidal configuration, with the corners thereof rounded off. The configuration of rigid plate 350 coincides with the configuration of the body's proximal surface 315, except that it is sized slightly smaller than proximal surface 315, in the manner shown in FIGS. 4 and 5.

A hole 355 extends through rigid plate 350. Hole 355 is coaxially aligned with the bore 340 extending through body 310, and is sized so as to have a diameter larger than the outer diameter of a cement dispenser's nozzle, as will hereinafter be disclosed in further detail. Preferably, hole 355 is sized so as to have a diameter larger than the diameter of the soft body's chamfered entryway 345, in the manner shown in FIGS. 4 and 5.

Bone canal pressurizer 305 may be sized as required for a particular application. In general, however, pressurizer 305 is sized so that its rigid plate 350 is longer and wider than the open end of the bone canal which is to receive the bone cement, and so that its distal surface 320 has a diameter less than the internal diameter of that bone canal. In this way the pressurizer's distal surface 320 can reside inside the bone canal, the pressurizer's inclined side wall 325 can engage the end surface of the bone, and the pressurizer's rigid plate 350 can be used to maintain the pressurizer in sealing engagement with the bone.

By way of example but not limitation, in the case of pressurizers to be used in hip replacement operations, and more specifically for use in injecting cement into the intramedullary canal of the femur of an adult, the following has been found to be appropriate: a length, as measured along the dimension A in FIG. 4, of about 2 inches; a width, as measured along the dimension B in FIG. 4, of about 1½ inches; a length, as measured along the dimension C in FIG. 6, of about ⅝ inch; a height, as measured along the dimension D in FIG. 5, of about ⅞ inch; a bore diameter, as measured along the dimension E in FIG. 5, of about ¼ inch; and a hole diameter, as measured along the dimension F in FIG. 5, of about 7/16 inch. Preferably the pressurizer's planar distal surface 320 is centered, in a widthwise sense, relative to proximal surface 315, whereby the dimension G in FIG. 4 will be about ¾ inch; and preferably the pressurizer's planar distal surface 320 is offset, in a lengthwise sense, relative to proximal surface 315, whereby the dimension H in FIG. 6 will be about ¾ inch and the dimension I in FIG. 6 will be about 1¼ inch.

Figure 7:
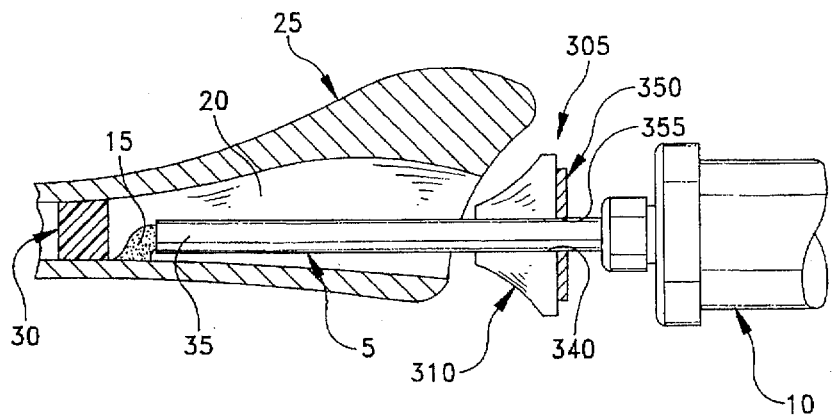
FIGS. 7-9 are schematic side views, partially in section, showing the bone canal pressurizer of the present invention being used to pressurize bone cement in a bone canal in accordance with one mode of use.
Figure 8:
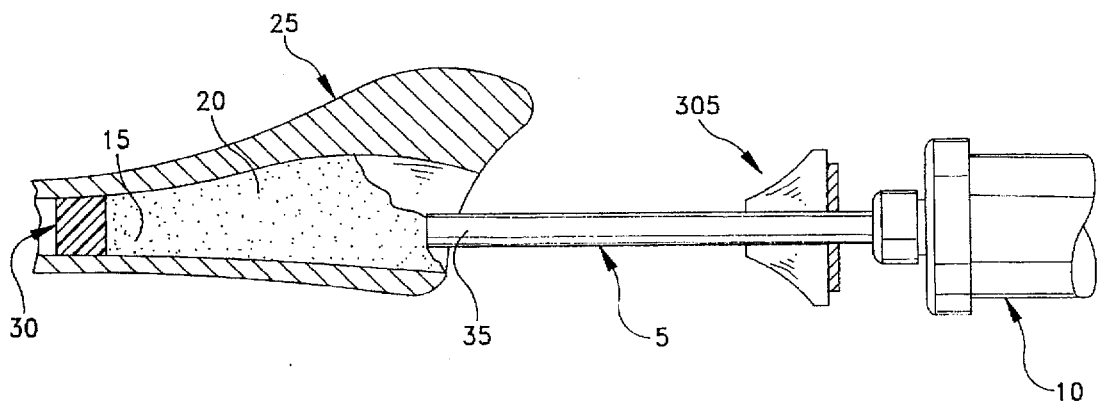
Figure 9:
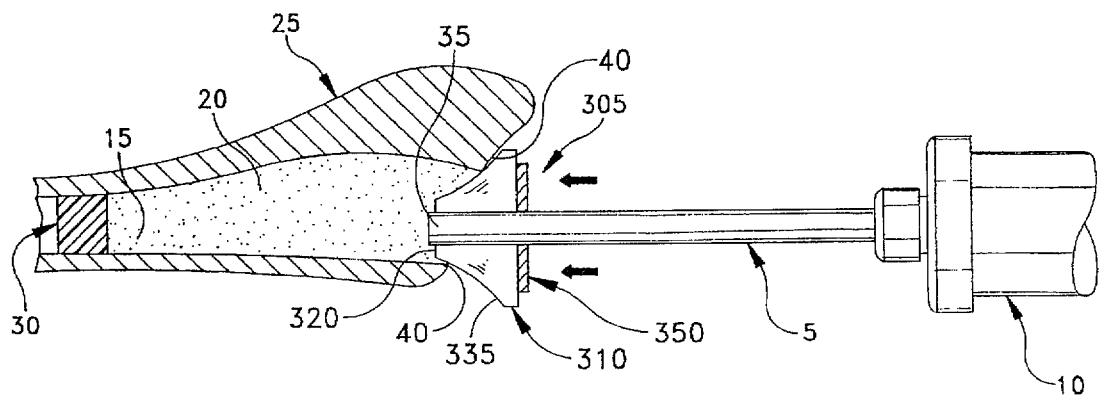

Referring next to FIGS. 7-9, in one manner of use bone canal pressurizer 305 is intended to be used as follows. First, the distal end 35 of nozzle 5 of cement dispenser 10 is passed through the pressurizer's hole 355 and bore 340 so that the distal end of the nozzle protrudes from the distal end of the pressurizer and the pressurizer sits adjacent to the cement dispenser, with the nozzle of the cement dispenser substantially fully exposed (see FIG. 7). It will be appreciated that, as this occurs, the cement dispenser's nozzle 5 will pass easily through the pressurizer's hole 355, since hole 355 is oversized relative to the nozzle. At the same time, nozzle 5 will firmly engage the pressurizer's soft foam body 310 as it passes through bore 340, since bore 340 is undersized relative to the nozzle. However, inasmuch as body 310 is formed out of a soft foam material, nozzle 5 will cause bore 340 to expand to the size of the nozzle, thereby forming a tight seal between nozzle 5 and pressurizer 305. The pressurizer is kept mounted on the proximal end of nozzle 5 while the nozzle is used to fill bone canal 20 of bone 25 with cement in the retrograde fashion previously described (see FIGS. 7 and 8).

When bone canal 20 is substantially completely filled with cement, pressurizer 305 is slid down the length of the nozzle's shaft to engage the open end of bone 25. In particular, pressurizer 305 is placed against the open end 40 (FIG. 9) of bone 25 so that (i) the pressurizer's distal surface 320 resides inside the bone's intramedullary canal 20, (ii) the pressurizer's inclined portion 335 engages the end surface 40 of the bone, and (iii) pressurizer's bore 340 and hole 355 are substantially aligned with the longitudinal axis of the bone canal. Pressure thereafter manually applied to the pressurizer's rigid plate 350 will cause a portion of the pressurizer's soft foam body 310 to wedge itself in the bone canal, whereby to form a tight seal between the inclined side wall portion 335 of the pressurizer and end surface 40 of bone 25. Additional bone cement may then be injected into the canal under pressure, without cement spilling out between the pressurizer and the bone or between the pressurizer and the nozzle.

Significantly, since the diameter of hole 355 in the pressurizer's rigid plate 350 is deliberately oversized relative to the outer diameter of the nozzle, and since the pressurizer's body 310 is formed out of soft foam, the surgeon may move the distal tip 35 of nozzle 5 about, without undermining the integrity of the pressurizer's seal with the bone or the pressurizer's seal with the nozzle, so as avoid soft tissue (such as the gluteal muscles) or bony obstructions (such as the greater trochanter) while injecting cement into the bone canal under pressure.

Figure 10:
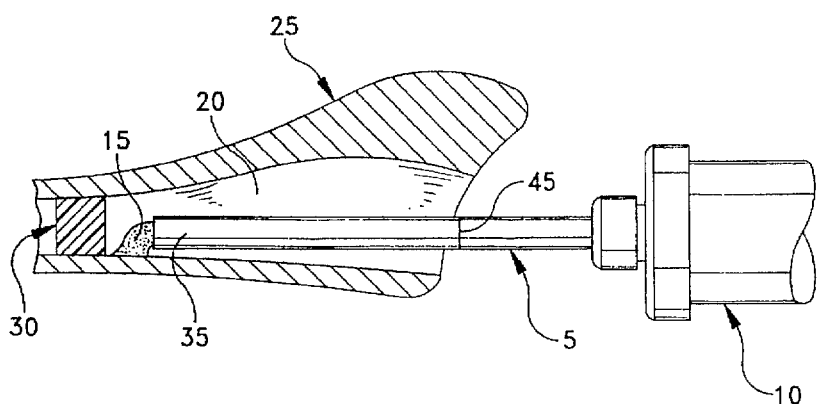
FIGS. 10-13 are schematic side views, partially in section, showing the bone canal pressurizer of the present invention being used to pressurize bone cement in a bone canal in accordance with an alternative mode of use.
Figure 11:
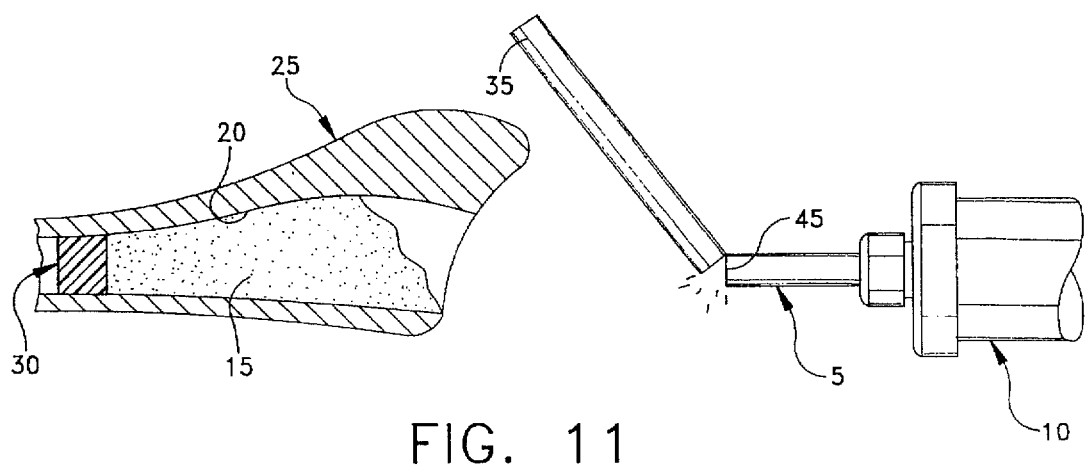
Figure 12:
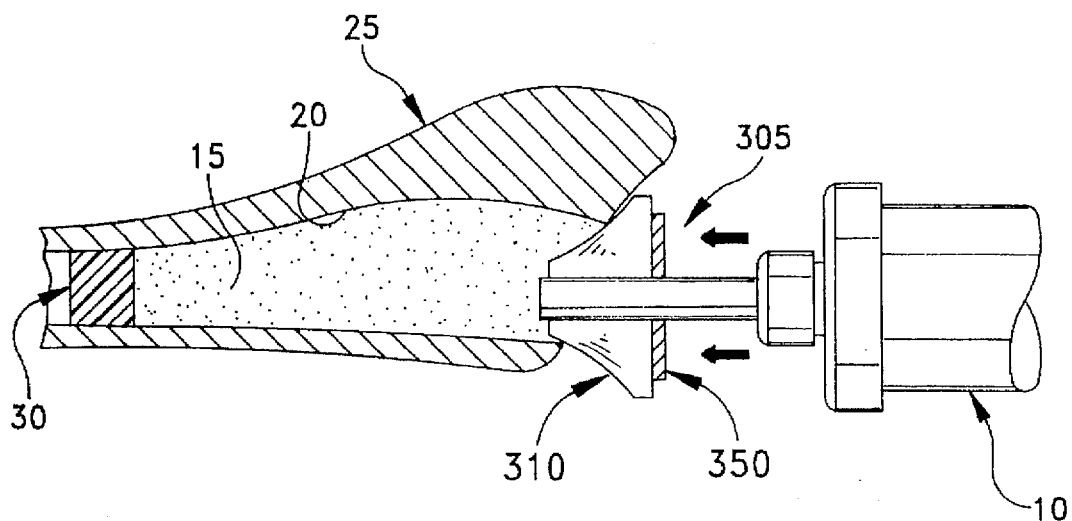

An alternative manner of use is shown in FIGS. 10–13. More particularly, in this alternative manner of use, pressurizer 305 is left initially dismounted from the nozzle of the cement dispenser while the nozzle is used to fill the bone canal with cement in the traditional retrograde manner described above (FIG. 10). After the bone canal has been completely filled with cement, nozzle 5 of cement dispenser 10 is withdrawn from the bone canal. Nozzle 5 is then preferably shortened in length by snapping off the distal end of the nozzle using a score line 45 which is provided for this purpose (FIGS. 10 and 11). Next, pressurizer 305 is mounted on the shortened nozzle, and the nozzle and pressurizer are moved as a single unit toward the open end of the bone, whereupon the nozzle will enter the interior of the bone canal as the pressurizer seats itself against the open end of the bone. With the pressurizer then manually held against the open end of the bone so as to seal off the bone canal, the cement dispenser can be used to inject additional cement into the bone canal under pressure (FIG. 12).

Again, it is to be appreciated that inasmuch as the diameter of hole 355 in the pressurizer's rigid plate 350 is deliberately oversized relative to the outer diameter of the nozzle, and inasmuch as the pressurizer's body 310 is formed out of soft foam, the surgeon may move the remaining portion of nozzle 5 and the cement dispenser 10 about, without undermining the integrity of the pressurizer's seal with the bone or the pressurizer's seal with the nozzle, so as to avoid soft tissue or bony obstructions while injecting cement into the bone canal under pressure.

Figure 13:
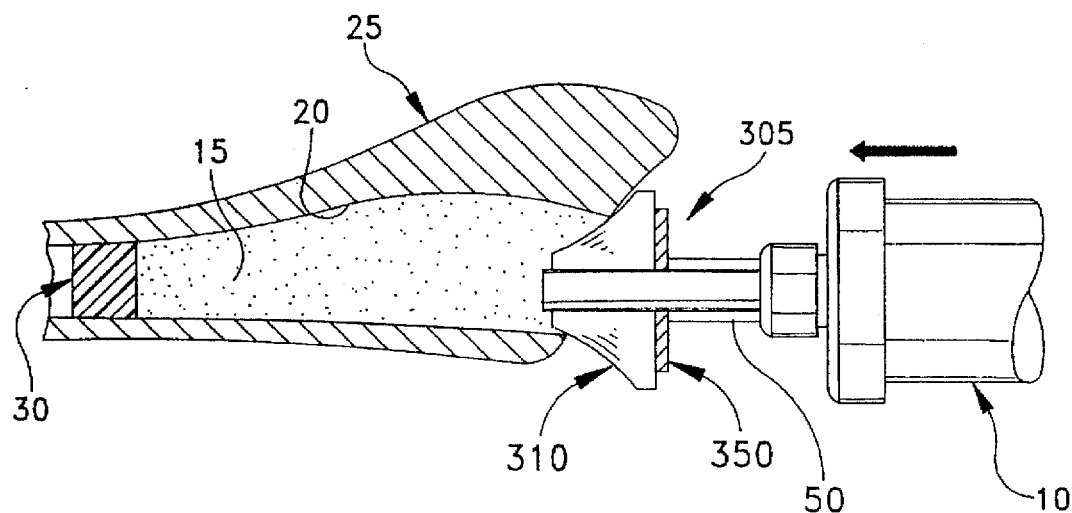

Furthermore, if one-handed operation is desired, a sleeve 50 can be provided on the proximal end of nozzle 5 so that manual pressure applied to the cement dispenser will be automatically transferred to the pressurizer so as to keep it in engagement with bone 25 (FIG. 13).

It will be appreciated that the principles and features of the present invention may be employed in various and numerous embodiments without departing from the scope of the invention. Thus it will be understood that the present invention is by no means limited to the particular construction herein disclosed and/or shown in the drawings, but also comprises any modifications or equivalents within the scope of the claims.

ADVANTAGE OF THE INVENTION

Numerous advantages are achieved through the use of the present invention.

For one thing, the present invention provides an improved bone canal pressurizer which is convenient to use.

For another thing, the present invention provides an improved bone canal pressurizer which is adapted to make an effective seal with a bone, whereby the pressurizer can serve to seal off the open end of a bone canal into which bone cement is to be injected under pressure.

And the present invention provides an improved bone canal pressurizer which is adapted to fit around, and make an effective seal with, the nozzle of a bone cement dispenser, whereby the nozzle of the cement dispenser can be used to inject bone cement under pressure into the interior of a bone canal.

Also, the present invention provides an improved bone canal pressurizer which facilitates angular movement of a cement dispenser and its nozzle to avoid soft tissue and/or bony obstructions even while the pressurizer is sealing off the open end of a bone.

Furthermore, the present invention provides an improved bone canal pressurizer which is adapted to fit around the nozzle of a bone cement dispenser and which can provide a reliable seal between the pressurizer and a bone, and between the pressurizer and the cement dispenser's nozzle, yet still permit maneuvering of the nozzle relative to both the pressurizer and the bone.

Also, the present invention provides an improved canal pressurizer wherein a single pressurizer can be used in conjunction with a variety of different bone sizes and shapes, so as to eliminate the need to provide the surgeon with a set having a range of different sized pressurizers.

And the present invention provides an improved method for dispensing bone cement into the interior of a bone canal under pressure.

What is claimed is:

1. A bone canal pressurizer for use in conjunction with the nozzle of a bone cement dispenser for compacting bone cement into the bone canal of a bone, said bone canal pressurizer comprising:

a body of soft foam material, said body having a planar proximal surface and a planar distal surface, said planar surfaces being parallel, said proximal surface having a greater surface area than said distal surface, and a side wall extending between said proximal surface and said distal surface, said side wall including a base portion normal to said proximal surface and an inclined portion extending from an edge of said base portion to said distal surface, said body defining a bore extending from said proximal surface to said distal surface, said bore having a diameter smaller than the outer diameter of the cement dispenser's nozzle; and a rigid plate fixed to said proximal surface and having a hole extending therethrough, said hole being aligned with said bore extending through said body, and said hole having a diameter larger than the outer diameter of said cement dispenser's nozzle, said plate having planar and parallel distal and proximal surfaces, said plate proximal surface being devoid of protrusions extending therefrom so as to be configured to receive in abutting engagement a cement dispenser portion there against, an outer edge of said plate being spaced inwardly from said body side wall base portion and being normal to said body proximal surface;

said distal surface of said body being sized so as to be small enough to fit within the bone canal of a bone, and said rigid plate being sized so as to be larger than the bone canal of that same bone.

2. A pressurizer according to claim 1 wherein said distal surface has a rounded configuration.

3. A pressurizer according to claim 2 wherein said distal surface has a circular configuration.

4. A pressurizer according to claim 1 wherein said proximal surface has a trapezoidal configuration, with rounded off corners.

5. A pressurizer according to claim 1 wherein said plate has a trapezoidal configuration, with rounded off corners.

6. A pressurizer according to claim 1 wherein the central axis of said bore is substantially centered across the widths of said proximal surface and said distal surface.

7. A pressurizer according to claim 1 wherein the central axis of said bore is spaced from a central portion of said body proximal surface, along the length of said body proximal surface and is substantially central of said body distal surface.

8. A pressurizer according to claim 1 wherein said body is chamfered at the point at which said bore meets said proximal surface.

9. A method for dispensing bone cement into a bone canal of a bone, said method comprising the steps of:

providing a cement dispenser including a nozzle for conveying the bone cement from a cement reservoir in said dispenser to the distal end of said nozzle;

said nozzle being adapted to be snapped off to shorten the length of said nozzle;

providing a bone canal pressurizer comprising:
 a body of soft foam material, said body having a planar proximal surface and a planar distal surface, said proximal surface having a greater surface area than said distal surface, and an inclined side wall extending between said proximal surface and said distal surface, said body defining a bore extending from said proximal surface to said distal surface, said bore having a diameter smaller than the outer diameter of the cement dispenser's nozzle; and a rigid plate fixed to said proximal surface and having a hole extending therethrough, said hole being aligned with said bore extending through said body, and said hole having a diameter larger than the outer diameter of said cement dispenser's nozzle;

said distal surface of said body being sized so as to be small enough to fit within the bone canal of a bone, and said rigid plate being sized so as to be larger than the bone canal of that same bone;

urging said distal surface of said body into the bone canal;

snapping off a portion of said nozzle of said cement dispenser to shorten the length of said nozzle;

moving said nozzle through said hole in said plate and through said bore in said body, until said body is wedged in said bone canal and the distal end of said nozzle is positioned in said bone canal; and manipulating said nozzle as desired within the bone canal and ejecting the cement into the bone canal.

10. A method according to claim 9 wherein said pressurizer is urged into said bone canal before said nozzle is moved through said pressurizer.

11. A method according to claim 9 wherein said nozzle is moved through said pressurizer before said pressurizer is urged into said bone canal.

* * * * *